US008569203B2

(12) United States Patent
Weiner et al.

(10) Patent No.: US 8,569,203 B2
(45) Date of Patent: *Oct. 29, 2013

(54) PROCESSES FOR MAKING TIN-CONTAINING CATALYSTS

(75) Inventors: Heiko Weiner, Pasadena, TX (US); Radmila Jevtic, Pasadena, TX (US); Victor Johnston, Houston, TX (US)

(73) Assignee: Celanese International Corporation, Irving, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/487,728

(22) Filed: Jun. 4, 2012

(65) Prior Publication Data
US 2012/0245022 A1   Sep. 27, 2012

Related U.S. Application Data

(63) Continuation of application No. 12/697,781, filed on Feb. 1, 2010, now Pat. No. 8,211,821.

(51) Int. Cl.
*B01J 23/00* (2006.01)

(52) U.S. Cl.
USPC .......................................................... 502/349

(58) Field of Classification Search
None
See application file for complete search history.

(56) References Cited

U.S. PATENT DOCUMENTS

| | | | |
|---|---|---|---|
| 2,021,698 A | 11/1935 | Perkins | |
| 2,105,540 A | 1/1938 | Lazier | |
| 2,607,807 A | 8/1952 | Ford | |
| 2,744,939 A | 5/1956 | Kennel | |
| 2,882,244 A | 4/1959 | Milton | |
| 3,130,007 A | 4/1964 | Breck | |
| 3,409,578 A * | 11/1968 | Hwa | 524/398 |
| 3,478,112 A | 11/1969 | Karl et al. | |
| 3,531,543 A * | 9/1970 | Clippinger et al. | 585/660 |
| 3,702,886 A | 11/1972 | Argauer et al. | |
| 3,729,429 A | 4/1973 | Robson | |
| 4,065,512 A | 12/1977 | Cares | |
| 4,070,272 A * | 1/1978 | Rausch | 208/217 |
| 4,228,307 A | 10/1980 | Zimmerschied | |
| 4,270,015 A | 5/1981 | Knifton et al. | |
| 4,275,228 A | 6/1981 | Gruffaz et al. | |
| 4,317,918 A | 3/1982 | Takano et al. | |
| 4,337,351 A | 6/1982 | Larkins | |
| 4,374,265 A | 2/1983 | Larkins, Jr. | |
| 4,395,576 A | 7/1983 | Kwantes et al. | |
| 4,398,039 A | 8/1983 | Pesa et al. | |
| 4,399,305 A | 8/1983 | Schreck et al. | |
| 4,421,939 A | 12/1983 | Kiff et al. | |
| 4,443,639 A | 4/1984 | Pesa et al. | |
| 4,465,854 A | 8/1984 | Pond et al. | |
| 4,471,136 A | 9/1984 | Larkins et al. | |
| 4,480,115 A | 10/1984 | McGinnis | |
| 4,517,391 A | 5/1985 | Schuster et al. | |
| 4,521,630 A | 6/1985 | Wattimena et al. | |
| 4,550,185 A | 10/1985 | Mabry et al. | |
| 4,581,473 A | 4/1986 | Polichnowski et al. | |
| 4,613,700 A | 9/1986 | Maki et al. | |
| 4,620,050 A | 10/1986 | Cognion et al. | |
| 4,678,543 A | 7/1987 | Houben et al. | |
| 4,692,218 A | 9/1987 | Houben et al. | |
| 4,710,086 A | 12/1987 | Naaktgeboren et al. | |
| 4,777,303 A | 10/1988 | Kitson et al. | |
| 4,804,791 A | 2/1989 | Kitson et al. | |
| 4,826,795 A | 5/1989 | Kitson et al. | |
| 4,843,170 A | 6/1989 | Isshiki et al. | |
| 4,886,905 A | 12/1989 | Larkins et al. | |
| 4,902,823 A | 2/1990 | Wunder et al. | |
| 4,978,778 A | 12/1990 | Isshiki et al. | |
| 4,985,572 A | 1/1991 | Kitson et al. | |
| 4,990,655 A | 2/1991 | Kitson et al. | |
| 5,061,671 A | 10/1991 | Kitson et al. | |
| 5,137,861 A | 8/1992 | Shih et al. | |
| 5,149,680 A | 9/1992 | Kitson et al. | |
| 5,155,084 A | 10/1992 | Horn et al. | |
| 5,185,308 A | 2/1993 | Bartley et al. | |
| 5,200,382 A | 4/1993 | Cody et al. | |
| 5,241,106 A | 8/1993 | Inoue et al. | |
| 5,243,095 A | 9/1993 | Roberts et al. | |
| 5,306,845 A | 4/1994 | Yokohama et al. | |
| 5,350,504 A | 9/1994 | Dessau | |
| 5,426,246 A | 6/1995 | Nagahara et al. | |

(Continued)

FOREIGN PATENT DOCUMENTS

EP          0104197          4/1984
EP          0137749          4/1985

(Continued)

OTHER PUBLICATIONS

Isli, et al., "The effect of lanthanum and barium additives on the thermal stabilization of gamma alumina", 1998, Turk J. Chem., pp. 253-260.

T. Yokoyama, et al., "Carboxylic Acids and Derivatives", Fine Chemicals through Heterogenous Catalysis, pp. 370-379.

Zheng, et al. (2007). Preparation and catalytic properties of a bimetallic Sn-Pt complex in the supercages of NaY zeolite by use of surface organometallic chemistry, Applied Organometallic Chemistry, 21(10), 836-840.

(Continued)

*Primary Examiner* — Melvin C Mayes
*Assistant Examiner* — Stefanie Cohen

(57) ABSTRACT

A process for producing a catalyst comprising the steps of contacting a support with a mixed metal precursor comprising tin oxalate, a second metal precursor, a solubilizing agent such as ammonium oxalate, and water to form an impregnated support and heating the impregnated support under conditions effective to remove at least a weight majority of the water and reduce the tin from the tin oxalate and the second metal from the second metal precursor and thereby form the catalyst.

20 Claims, No Drawings

(56) References Cited

U.S. PATENT DOCUMENTS

| | | |
|---|---|---|
| 5,475,144 A | 12/1995 | Watson et al. |
| 5,476,827 A | 12/1995 | Ferrero et al. |
| RE35,377 E | 11/1996 | Steinberg et al. |
| 5,585,523 A | 12/1996 | Weiguny et al. |
| 5,691,267 A | 11/1997 | Nicolau et al. |
| 5,719,315 A | 2/1998 | Tustin et al. |
| 5,731,456 A | 3/1998 | Tustin et al. |
| 5,767,307 A | 6/1998 | Ramprasad et al. |
| 5,821,111 A | 10/1998 | Gaddy et al. |
| 5,849,657 A | 12/1998 | Rotgerink et al. |
| 5,861,530 A | 1/1999 | Atkins et al. |
| 5,935,889 A | 8/1999 | Murrell et al. |
| 5,945,570 A | 8/1999 | Arhancet et al. |
| 5,955,397 A | 9/1999 | Didillon et al. |
| 5,973,193 A | 10/1999 | Crane et al. |
| 6,040,474 A | 3/2000 | Jobson et al. |
| 6,049,008 A | 4/2000 | Roberts et al. |
| 6,093,845 A | 7/2000 | Van Acker et al. |
| 6,114,571 A | 9/2000 | Abel et al. |
| 6,121,498 A | 9/2000 | Tustin et al. |
| 6,232,352 B1 | 5/2001 | Vidalin et al. |
| 6,232,504 B1 | 5/2001 | Barteau et al. |
| 6,281,160 B1 | 8/2001 | Basset |
| 6,294,703 B1 | 9/2001 | Hara et al. |
| 6,417,133 B1 | 7/2002 | Ebner et al. |
| 6,462,231 B1 | 10/2002 | Yanagawa et al. |
| 6,472,555 B2 | 10/2002 | Choudary et al. |
| 6,486,366 B1 | 11/2002 | Ostgard et al. |
| 6,509,180 B1 | 1/2003 | Verser et al. |
| 6,559,333 B1 | 5/2003 | Brunelle et al. |
| 6,603,038 B1 | 8/2003 | Hagemeyer et al. |
| 6,632,330 B1 | 10/2003 | Colley et al. |
| 6,693,213 B1 | 2/2004 | Kolena et al. |
| 6,696,596 B1 | 2/2004 | Herzog et al. |
| 6,727,380 B2 | 4/2004 | Ellis et al. |
| 6,765,110 B2 | 7/2004 | Warner et al. |
| 6,768,021 B2 | 7/2004 | Horan et al. |
| 6,812,372 B2 | 11/2004 | Janssen et al. |
| 6,852,877 B1 | 2/2005 | Zeyss et al. |
| 6,903,045 B2 | 6/2005 | Zoeller et al. |
| 6,906,228 B2 | 6/2005 | Fischer et al. |
| 6,927,048 B2 | 8/2005 | Verser et al. |
| 7,074,603 B2 | 7/2006 | Verser et al. |
| 7,084,312 B1 | 8/2006 | Huber et al. |
| 7,297,236 B1 | 11/2007 | Vander Griend et al. |
| 7,351,559 B2 | 4/2008 | Verser et al. |
| 7,375,049 B2 | 5/2008 | Hayes et al. |
| 7,425,657 B1 | 9/2008 | Elliott et al. |
| 7,507,562 B2 | 3/2009 | Verser et al. |
| 7,518,014 B2 | 4/2009 | Kimmich et al. |
| 7,538,060 B2 | 5/2009 | Barnicki et al. |
| 7,553,397 B1 | 6/2009 | Colley et al. |
| 7,572,353 B1 | 8/2009 | Vander et al. |
| 7,608,744 B1 | 10/2009 | Johnston et al. |
| 7,863,489 B2 | 1/2011 | Johnston et al. |
| 2001/0048970 A1 | 12/2001 | Hagemeyer et al. |
| 2003/0013908 A1 | 1/2003 | Horan et al. |
| 2003/0077771 A1 | 4/2003 | Verser et al. |
| 2003/0104587 A1 | 6/2003 | Verser et al. |
| 2003/0114719 A1 | 6/2003 | Fischer et al. |
| 2003/0191020 A1 | 10/2003 | Bharadwaj et al. |
| 2004/0195084 A1 | 10/2004 | Hetherington et al. |
| 2004/0232049 A1 | 11/2004 | Dath et al. |
| 2005/0181940 A1 | 8/2005 | Wang et al. |
| 2006/0102520 A1 | 5/2006 | Lapinski |
| 2006/0127999 A1 | 6/2006 | Verser et al. |
| 2007/0106246 A1 | 5/2007 | Modesitt |
| 2007/0238605 A1 | 10/2007 | Strehlau et al. |
| 2008/0207953 A1 | 8/2008 | Houssin et al. |
| 2008/0227627 A1 | 9/2008 | Strehlau et al. |
| 2008/0257784 A1 | 10/2008 | Dath et al. |
| 2009/0005588 A1 | 1/2009 | Hassan et al. |
| 2009/0023192 A1 | 1/2009 | Verser et al. |
| 2009/0166172 A1 | 7/2009 | Casey et al. |
| 2009/0221725 A1 | 9/2009 | Chornet et al. |
| 2009/0326080 A1 | 12/2009 | Chorney et al. |
| 2010/0016454 A1 | 1/2010 | Gracey et al. |
| 2010/0029995 A1 | 2/2010 | Johnston et al. |
| 2010/0113843 A1 | 5/2010 | Lee et al. |
| 2010/0121114 A1 | 5/2010 | Weiner et al. |
| 2010/0168493 A1 | 7/2010 | Le Peltier et al. |
| 2010/0196789 A1 | 8/2010 | Fisher et al. |
| 2010/0249479 A1 | 9/2010 | Berg-Slot et al. |

FOREIGN PATENT DOCUMENTS

| | | |
|---|---|---|
| EP | 0167300 | 1/1986 |
| EP | 0175558 | 3/1986 |
| EP | 0192587 | 8/1986 |
| EP | 0198682 | 10/1986 |
| EP | 0285420 | 10/1988 |
| EP | 0285786 | 10/1988 |
| EP | 0330853 | 9/1989 |
| EP | 0400904 | 5/1990 |
| EP | 0372847 | 6/1990 |
| EP | 0408528 | 7/1990 |
| EP | 1277826 | 1/2003 |
| EP | 2060553 | 5/2009 |
| EP | 2060555 | 5/2009 |
| EP | 2186787 | 5/2010 |
| GB | 1168785 | 10/1969 |
| GB | 1559540 | 1/1980 |
| GB | 2136704 | 9/1984 |
| JP | 10-306047 | 11/1998 |
| JP | 2001-046874 | 2/2001 |
| JP | 2001-157841 | 6/2001 |
| WO | WO 83/03409 | 10/1983 |
| WO | WO 03/040037 | 5/2003 |
| WO | WO 2005/102513 | 11/2005 |
| WO | WO 2007/107371 | 9/2007 |
| WO | WO 2009/009322 | 1/2009 |
| WO | WO 2009/009323 | 1/2009 |
| WO | WO 2009/063176 | 5/2009 |
| WO | WO 2009/105860 | 9/2009 |
| WO | WO 2010/014151 | 2/2010 |
| WO | WO 2010/055285 | 5/2010 |

OTHER PUBLICATIONS

ZeaChem, Inc., Technology Overview, Lakewood, Colorado www.zeachem.com, 2008.

Santori et al.(2000). Hydrogenation of carbonylic compounds on Pt/SiO2 catalysts modified with SnBu4, Studies in Surface Science and Catalysis, 130, 2063-2068.

Rachmady, Acetic Acid Reduction by H2 on Bimetallic Pt—Fe Catalysts, Journal of Catalysis 209, 87-98 (Apr. 1, 2002), Elsevier Science (USA).

Pestman et al., The formation of ketones and aldehydes from carboxylic acids, structure-activity relationship for two competitive reactions, Journal of Molecular Catalysis A: Chemical 103 Jun. 14, 1995, 175-180.

Proc. Roy Soc. A314, pp. 473-498 (1970).

Gursahani et al., Reaction kinetics measurements and analysis of reaction pathways for conversions of acetic acid, ethanol, and ethyl acetate over silica-supported Pt, Applied Catalysis A: General 222 (2001) 369-392.

Brunauer Emmett and Teller, J. Am. Chem. Soc. 60, 309 (1938).

Alcala, et al., (2005). Experimental and DFT studies of the conversion of ethanol and acetic acid on PtSn-based catalysts, Journal of Physical Chemistry, 109(6), 2074-2085.

Audebrand, et al., "Synthesis, open-framework structure and thermal behavior of ammonium tin oxalate, $Sn_2(NH_4)_2(C_2O_4)_3 \cdot 3H_2O$", Elsevier, Solid State Sciences, (2001), pp. 483-494.

International Search Report and Written Opinion for PCT/US2011/023230 mailed May 3, 2011.

International Preliminary Report on Patentability for PCT/US2011/023230 mailed Aug. 16, 2012.

* cited by examiner

PROCESSES FOR MAKING TIN-CONTAINING CATALYSTS

CROSS REFERENCE TO RELATED APPLICATIONS

This application is a continuation application of U.S. application Ser. No. 12/697,781, filed Feb. 1, 2010, the entire contents and disclosures of which are incorporated herein by reference.

FIELD OF THE INVENTION

The present invention relates to processes for manufacturing catalysts that may be used, for example, in the hydrogenation of carboxylic acids such as acetic acid. More specifically, the invention relates to the use of solubilizing agents to form mixed metal precursors for use in producing tin-containing hydrogenation catalysts, optionally in a one step support impregnation process.

BACKGROUND OF THE INVENTION

There has been a long felt need for an economically viable process to convert acetic acid to ethanol, which may be used outright or subsequently converted to one or more derivative products such as ethylene. Ethylene is an important commodity feedstock because it can be converted to polyethylene, vinyl acetate, ethyl acetate, or any of a wide variety of other chemical products such as monomer and polymer products. Fluctuating natural gas and crude oil prices contribute to variances in the cost of ethylene conventionally produced therefrom. Thus, the need for alternative sources of ethylene is especially evident when oil prices rise.

Catalytic processes for reducing carboxylic acids, e.g., acetic acid, and other carbonyl group containing compounds have been widely studied. The literature is replete with various combinations of catalysts, supports, and operating conditions for such processes. For example, the reduction of various carboxylic acids over metal oxides is reviewed by T. Yokoyama et al., in which the authors summarize some of the developmental efforts for hydrogenation catalysts for various carboxylic acids. (Yokoyama, T.; Setoyama, T. "Fine chemicals through heterogeneous catalysis. Carboxylic acids and derivatives," 2001, 370-379, which is incorporated herein by reference in its entirety). It has been difficult, however, to achieve the desired hydrogenation products with conventional catalysts and supports. In some cases, for example, conversion of acetic acid to the desired hydrogenation product is low, while in other cases, selectivity of the desired product, based on the amount of converted acetic acid, is undesirably low.

As one potential solution to this problem, multi-metallic, e.g., bimetallic, catalysts have been suggested for catalyzing the hydrogenation of acetic acid to form products such as ethanol. As one particular example, bimetallic catalysts comprising tin and a second metal have been utilized in ethanol formation. These bimetallic catalysts are typically formed by contacting multiple metal precursors, e.g., a tin precursor and a second metal precursor, with a suitable support in multiple contacting steps and reducing the metal precursors, typically in separate heating steps, in order to impregnate the support with the two metals. Such synthesis processes are undesirable and inefficient, however, due to the required multiple impregnation steps.

A simplified approach for forming bimetallic catalysts involves impregnating a support with multiple metal precursors in a single impregnation step followed by heating to reduce the metal precursors to their corresponding metals. Such single step impregnation processes, however, are not suitable for all metal precursors since some metal precursors are not compatible with one another. This is particularly true of tin precursors, such as tin oxalate, which are generally of low solubility and incompatible with aqueous-based metal precursors.

Thus, the need exists for simplified and efficient processes for forming bimetallic catalysts that include tin.

SUMMARY OF THE INVENTION

The present invention relates to processes for forming catalysts, e.g., hydrogenation catalysts, comprising tin and a second metal on a support. The invention also relates to mixed metal precursor compositions useful for forming such catalysts without the need for halogenated metal precursors (i.e. chlorides).

In one embodiment, for example, the invention is to a process for producing a catalyst, the process comprising the steps of: (a) contacting, optionally through incipient wetness techniques, a support with a mixed metal precursor comprising the reaction product of tin oxalate, a second metal precursor, a solubilizing agent, and water to form an impregnated support; and (b) heating the impregnated support, e.g., to a temperature from 120° C. to 200° C., under conditions effective to remove at least a weight majority of the water and reduce the tin from the tin oxalate and the second metal from the second metal precursor and form the catalyst. The heating step preferably occurs under a reducing atmosphere at least in part. For example, the heating step optionally comprises a drying step and a reducing step. The process optionally further comprises the step of forming the mixed metal precursor by combining the tin oxalate, the second metal precursor, the solubilizing agent and the water.

The contacting step may occur in a single step or, if desired, in multiple contacting steps, if, for example, it is desired to further impregnate the support with a third metal derived from a third metal precursor. In the latter embodiment, the process may further comprise the steps of: (c) contacting the support with a third metal precursor comprising a third metal not tin and different from the second metal; and (d) reducing the third metal precursor to form the third metal or its oxide on the support. Steps (c) and (d) may occur before or after steps (a) and (b).

Desirably, the solubilizing agent, e.g., ammonium oxalate, facilitates solubilizing of the tin oxalate in water, even at relatively low temperatures, e.g., at room temperature. Thus, in one aspect, the mixed metal precursor is at a temperature ranging from 10° C. to 50° C., e.g., from 20° C. to 30° C., during the contacting step.

Optionally, the process further comprises calcining the catalyst at a temperature from 225° C. to 500° C. to form a calcined catalyst. In other embodiments, no calcination is desired as the catalyst is suitable for use in a hydrogenation process to form ethanol at a selectivity greater than 80 wt. % without calcination.

In another embodiment, the invention is to the mixed metal precursor itself, e.g., as a solution. For example, in one aspect, the invention is to a mixed metal precursor, formed by combining (a) tin oxalate; (b) a second metal precursor; (c) a solubilizing agent; and (d) water. In still another embodiment, the invention is to the reaction product of tin oxalate, a second metal oxalate, and ammonium oxalate in water.

In each of these embodiments, the solubilizing agent may, for example, be a Group IA metal oxalate, ammonium oxalate, tetraalkyl ammonium oxalate or phosphonium oxalate.

The second metal precursor, which preferably is a second metal oxalate, comprises a second metal, which preferably is selected from the group consisting of platinum, iridium, rhodium, palladium, copper, cobalt, manganese, lead, chromium, thallium, iron, osmium, gold, silver, cadmium, rhenium, rhodium, and ruthenium. Most preferably, the second metal is platinum, and the second metal precursor comprises platinum oxalate.

Although the concentrations of the various components in the mixed metal precursor may vary widely depending, for example, on the desired composition for the ultimately formed catalyst, in some exemplary embodiments the mixed metal precursor comprises the tin oxalate at a theoretical concentration of from 0.01 M to 0.1 M, the second metal precursor at a theoretical concentration of from 0.01 M to 0.1 M, and the ammonium oxalate at a theoretical concentration of from 0.02 M to 0.32 M. The mixed metal precursor may comprise the ammonium oxalate and the tin oxalate at a molar ratio greater than 1:1, e.g., greater than 2:1.

The composition of the support may vary, but in some exemplary embodiments is selected from the group consisting of iron oxide, silica, alumina, silica/aluminas, titania, zirconia, magnesium oxide, calcium silicate, carbon, graphite, high surface area graphitized carbon, activated carbons, and mixtures thereof. Optionally, the support comprises a support material and a support modifier, e.g., an acid support modifier, a redox support modifier or a basic support modifier. The acidic or basic characteristics of the support may help determine how specific the resulting catalyst is for a particular product. For example, acidic supports may tend to favor formation of ethyl acetate from acetic acid, while more basic supports may tend to favor formation of ethanol from acetic acid. In a preferred embodiment, the support material comprises silica and the support modifier comprises calcium metasilicate.

DETAILED DESCRIPTION OF THE INVENTION

Introduction

Conventionally it has been difficult to hydrogenate alkanoic acids, e.g., acetic acid, to produce desired products, such as ethanol, with a desired level of conversion and/or selectivity to ethanol. To achieve the desired conversions and selectivities, bimetallic hydrogenation catalysts such as platinum/tin catalysts have been suggested. See, for example, jointly owned U.S. patent application Ser. Nos. 12/221,141 and 12/588,727, each of which is hereby incorporated by reference in its entirety. To date, however, it has been difficult to produce bimetallic catalysts starting from halogen-free metal precursors that comprise tin due to the incompatibility of tin precursors with many other metal precursors, and in particular with aqueous-based metal precursors since tin precursors such as tin oxalate or tin acetate are insoluble in water.

The present invention relates to effective processes for producing bimetallic catalysts that comprise tin and one or more additional metals. In particular, it has now been discovered that the presence of a solubilizing agent such as ammonium oxalate in a single mixed metal precursor may facilitate dissolution of organic tin precursors such as tin oxalate in water desirably rendering them compatible with other aqueous metal precursors, e.g., other metal oxalates such as platinum oxalate.

Thus, in one embodiment, the invention is directed to a process for producing a catalyst, the process comprising the steps of: (a) contacting a support with a mixed metal precursor comprising tin oxalate, a second metal precursor (preferably a second metal oxalate), a solubilizing agent such as ammonium oxalate, and water to form an impregnated support; and (b) heating the impregnated support under conditions effective to remove at least a weight majority of the water and reduce the tin from the tin oxalate and the second metal from the second metal precursor. Although not required, the process optionally further comprises a step of calcining the resulting catalyst to form a calcined catalyst composition.

Mixed Metal Precursor

As indicated above, the processes of the present invention involve the use of a mixed metal precursor that may be impregnated into a support, optionally a modified support, preferably in a single impregnation step. According to embodiments of the present invention, the mixed metal precursor is formed by combining tin oxalate, a second metal precursor (preferably platinum oxalate), a solubilizing agent (preferably ammonium oxalate), and water.

Without being bound by theory, it is believed that when ammonium oxalate and platinum oxalate are employed in the process and mixed metal precursors of the invention, the ammonium oxalate acts to facilitate solubilizing of the tin oxalate by forming dioxalatostannate and other tin oxalate species, as shown in the following reactions.

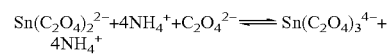

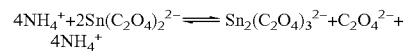

In addition, without being bound by theory, once the second metal precursor is added to the tin oxalate/ammonium oxalate solution, the second metal cation is reduced by the tin cations to form elemental nanoparticles of the second metal. This may be indicated by a color change in the mixed metal precursor. Surprisingly and unexpectedly, the ammonium oxalate desirably acts to stabilize the second metal nanoparticles. This sequence of reactions is shown below where the second metal precursor comprises platinum oxalate.

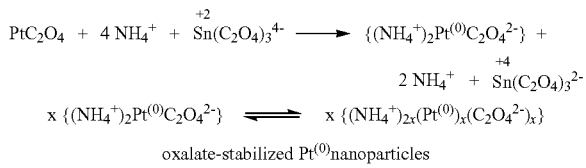

oxalate-stabilized Pt$^{(0)}$ nanoparticles

Thus, in another embodiment, the invention is directed to the reaction product of tin oxalate, a second metal precursor, preferably a second metal oxalate, and ammonium oxalate in water. Preferably, the second metal oxalate comprises platinum oxalate, although in other aspects the second metal oxalate may comprise a second metal selected from the group consisting of iridium, rhodium, palladium, copper, cobalt, manganese, lead, chromium, thallium, iron, osmium, gold, silver, cadmium, rhenium, rhodium, and ruthenium.

Generally, any order of addition of the various components to form the mixed metal precursor may be used so long as the resulting mixed metal precursor remains suitable to impregnate the desired support. In a preferred embodiment, an aqueous solution comprising water and the solubilizing agent, e.g., ammonium oxalate, is combined with solid tin oxalate, for example, in powder form. That is, the ammonium oxalate is dissolved in water and the resulting solution is added to the tin oxalate, or alternatively the solid tin oxalate may be added to the ammonium oxalate solution. The second metal precursor, e.g., platinum oxalate, may then be dissolved in water and added to the tin oxalate/ammonium oxalate mixture, or solid second metal precursor may be added to the aqueous tin oxalate/ammonium oxalate solution. Alternatively, the solubilizing agent may be added to the water after it is combined with the solid tin oxalate. In another aspect, solid tin oxalate is added to a solution comprising the second metal precursor, water, and the solubilizing agent. Optionally, the mixed metal precursor further comprises a third metal precursor, or additional metal precursors. Generally, the aqueous components of the mixed metal precursor are agitated as the mixed metal precursor is formed, although this is not required. Suitable agitation methods include mechanical (stirring), ultrasonic, or magnetic stirring.

However formed, the resulting mixed metal precursor beneficially comprises a tin precursor, e.g., tin oxalate, and the second metal precursor, preferably a second metal oxalate, in a single aqueous phase that is suitable for impregnating a support, optionally a modified support, in a single impregnation step thereby eliminating the necessity of separately impregnating the support with the two or more metals.

The mixed metal precursor may be formed at a variety of temperatures and optionally is formed at room temperature (25° C.). In some aspects, the mixed metal precursor is formed at a temperature ranging from 20° C. to 80° C., e.g., from 10° C. to 50° C., from 20° C. to 50° C. or from 20° C. to 30° C., or at a temperature less than 80° C., e.g., less than 75° C. or less than 50° C.

In addition to the tin oxalate, the second metal precursor, the water, and the solubilizing agent, the mixed metal precursor may further comprise one or more additives to modify one or more properties of the mixed metal precursor. Exemplary additives that may be included in the mixed metal precursor include one or more solubility modifiers, surfactants, acids, bases, and/or non-aqueous solvents.

The relative theoretical concentrations of the tin oxalate and the second metal precursor in the mixed metal precursor may vary widely, although the tin oxalate and the second metal precursor preferably are provided in amounts sufficient to form a catalyst having the desired molar ratio of tin to the second metal. Of course, the tin oxalate and second metal precursor preferably are provided in concentrations below their respective saturation limits. Generally, the tin oxalate and the second metal precursor may be provided in any amount so long as they remain in solution. For example, the concentrations of tin oxalate and second metal precursor in the mixed metal precursor optionally may be selected such that the total weight of tin and second metal (and optionally any additional metals) present in the resulting catalyst ranges from 0.1 to 25 wt %, e.g., from 0.5 to 15 wt %, or from 0.75 wt % to 10 wt %. In terms of individual theoretical concentrations, the mixed metal precursor optionally comprises the tin oxalate in a theoretical concentration of at least 0.001 M, e.g., at least 0.01 M or at least 0.05 M. In terms of ranges, the mixed metal precursor optionally comprises the tin oxalate at a theoretical concentration ranging from 0.001 M to 0.5 M, e.g., from 0.01 M to 0.1 M or from 0.04 M to 0.1 M. The mixed metal precursor optionally comprises the second metal precursor in a theoretical concentration of at least 0.001 M, e.g., at least 0.01 M or at least 0.05 M. In terms of ranges, the mixed metal precursor optionally comprises the second metal precursor in a theoretical concentration ranging from 0.001 M to 0.5 M, e.g., from 0.01 M to 0.1 M or from 0.04 M to 0.1 M. Preferably, the molar ratio of the tin to the second metal in the mixed metal precursor (without regard to corresponding anionic species), ranges from 3:1 to 1:3, e.g., from 2:1 to 1:2, or from 0.6:0.4 to 0.4:0.6. In a preferred embodiment, the mixed metal precursor comprises the tin oxalate at a theoretical concentration of from 0.01 M to 0.1 M, the second metal precursor at a theoretical concentration of from 0.01 M to 0.1 M, and the ammonium oxalate at a theoretical concentration of from 0.02 M to 0.32 M. By "theoretical concentration," it is meant the calculated concentration based on the moles of each component initially added to form the mixed metal precursor and the total volume of the mixed metal precursor without taking into consideration any change in actual concentration that may result from one or more of the tin oxalate, the second metal precursor and/or the solubilizing agent reacting with one another in the mixed metal solution.

As indicated above, in preferred embodiments of the invention, the solubilizing agent comprises an oxalate, e.g., a Group IA oxalate (e.g., sodium or potassium oxalate), ammonium oxalate, tetraalkyl ammonium oxalate or phosphonium oxalate. Thus, in some aspects, the solubilizing agent may comprise a quaternary amine or a phosphine. In preferred embodiments, the solubilizing agent comprises ammonium oxalate as indicated above. The ammonium oxalate may be in hydrated from, e.g., ammonium oxalate monohydrate $(NH_4)_2C_2O_4.H_2O$, although the anhydrous form may also be utilized. In other embodiments, a solubilizing agent other than ammonium oxalate is employed.

Although the amount of solubilizing agent in the mixed metal precursor may vary widely, the solubilizing agent preferably is present in an amount sufficient to solubilize the tin oxalate as well as any second metal nanoparticles formed in the mixed metal precursor. In some exemplary aspects, the mixed metal precursor comprises the ammonium oxalate in a theoretical concentration of at least 0.01 M, e.g., at least 0.02 M or at least 0.1 M. In terms of ranges, the mixed metal precursor optionally comprises the ammonium oxalate in a theoretical concentration ranging from 0.01 M to 0.5 M, e.g., from 0.02 M to 0.32 M, or from 0.1 M to 0.22 M. In some exemplary embodiment, the mixed metal precursor comprises the ammonium oxalate and the tin oxalate at a molar ratio greater than 1:1, e.g., greater than 2:1.

With regard to the second metal precursor, the term "second" is meant to indicate that the second metal is not tin. Similarly, if the mixed metal precursor comprises a third metal precursor (or additional metal precursors), the term "third" indicates that the third metal is a metal other than tin and different from the second metal. The second metal may vary widely, as long as it is not tin. In one embodiment, the second metal may be a Group IB, IIB, IIIB, IVB, VB, VIIB, VIIB, or VIII transitional metal, a lanthanide metal, an actinide metal or a metal from any of Groups IA, IIA, IIIA, IVA (excluding tin), VA, or VIA. Preferably, however, the second metal is selected from any metal that is more electropositive than tin(II), e.g., any metal that has a standard reduction potential greater than 0.15 eV. In preferred embodiments, the second metal is selected the group consisting of platinum, iridium, rhodium, palladium, copper, cobalt, manganese, lead, chromium, thallium, iron, osmium, gold, silver, cadmium, rhenium, rhodium, and ruthenium. Optionally, the second metal is selected from the group consisting of platinum, palladium, and ruthenium. Most preferably, the second metal is platinum. The second metal precursor preferably comprises a second metal oxalate of one or more of the following metals platinum, iridium, rhodium, palladium, copper, cobalt, manganese, lead, chromium, thallium, iron, osmium, gold, silver, cadmium, rhenium, rhodium, and ruthenium. Exemplary second metal precursors that may be included in the mixed metal precursor include, but are not limited to, chloroplatinic acid, ammonium chloroplatinate, amine solubilized platinum hydroxide, platinum nitrate, platinum tetra ammonium nitrate, platinum chloride, platinum oxalate, palladium nitrate, palladium tetra ammonium nitrate, palladium chloride, palladium oxalate, sodium palladium chloride, and sodium platinum chloride, although halide free precursors are preferred. Most preferably, the second metal precursor comprises platinum oxalate.

In one embodiment, as indicated above, the second metal precursor is a platinum precursor, e.g., platinum oxalate. In this embodiment, one or more additional platinum precursors, e.g., $Pt(NH_3)_4(NO_4)_2$, may be incorporated into the mixed metal precursor. In those cases where the catalyst is intended for use in forming ethanol at high selectivity, it is generally preferable to avoid the use of halogenated metal precursors.

As indicated above, in addition to the tin oxalate and the second metal precursor, the mixed metal precursor may further comprise one or more additional metal precursors. As an example, the mixed metal precursor may further comprise an additional metal precursor in solubilized form, e.g., one or more metal halides, amine solubilized metal hydroxides, metal nitrates or metal oxalates, dissolved in water. The metals mentioned above with respect to the second metal apply equally to any additional metals, so long as the second metal and the one or more additional metals are not the same and are not tin. In preferred aspects, the one or more additional metals (e.g., third metal, fourth metal, etc.) are selected from the group consisting of platinum, iridium, rhodium, palladium, copper, cobalt, manganese, lead, chromium, thallium, iron, osmium, gold, silver, cadmium, rhenium, rhodium, and ruthenium. Preferred trimetallic combinations for various embodiments of the invention are provided below in Table 1.

TABLE 1

Preferred Trimetallic Catalyst Compositions

| First Metal | Second Metal | Third Metal |
|---|---|---|
| Sn | Pt | Re |
| Sn | Pt | Cu |
| Sn | Pt | Co |
| Sn | Pt | Pd |
| Sn | Pt | Au |
| Sn | Pd | Re |
| Sn | Pd | Cu |
| Sn | Pd | Co |
| Sn | Pd | Au |
| Sn | Co | Re |
| Sn | Co | Cu |
| Sn | Co | Au |

Processes for Manufacturing Catalyst

Once the metal precursor has been formed, it preferably is impregnated onto a support, optionally a modified support, to form the desired catalyst composition. This process involved contacting, e.g., impregnating, the mixed metal precursor with the support under conditions effective to impregnate the support therewith. One important beneficial feature of the mixed metal precursor is that both the tin component and the second metal component are in the aqueous phase, e.g., the two metal components are not in two separate phases. As such, the inventive mixed metal precursor can be advantageously utilized to impregnate a suitable support with both tin and the second metal, e.g., in a single impregnation step.

Typically, the mixed metal precursor is added to the support and the support is allowed absorb the metal precursor. This may be done drop wise through incipient wetness techniques until complete impregnation of the support is substantially achieved. Alternatively, the support may be placed by aliquots or batch wise into the mixed metal precursor. A roto-immersion or other assistive apparatus may be used to achieve thorough contacting between the support and the mixed metal precursor. Further, a spray device may be used such that the mixed metal precursor is sprayed through a nozzle onto the support, where it absorbed. Optionally, decanting, heat, or reduced pressure may be used to remove any excess liquid not absorbed by the support or to dry the support after impregnation. The mixed metal precursor may be at or about room temperature during the contacting step. In an alternative embodiment, the mixed metal precursor may contact the support through a chemical vapor deposition process, such as described in US2001/0048970, which is hereby incorporated by reference in its entirety.

Once the mixed metal precursor has contacted and impregnated the support, optionally the modified support, the resulting impregnated support is heated under conditions effective to reduce the metal components of the tin oxalate and the second metal precursor to form elemental (or oxidic) tin and the second metal or second metal oxide on the support. The heating step may comprise a drying step or a reducing step or a single integrated drying/heating step.

Preferably, the heating step comprises a drying step, typically under air, in which at least a weight majority, e.g., more than 50 wt %, more than 80 wt. % or more than 90 wt. % of the water, is removed from the impregnated support, hence drying the catalyst composition. For example, the heating may be to a temperature greater than 100° C., e.g., greater than 120° C. or greater than 150° C. for a period of time ranging, for example, from 1 to 48 hours, e.g., from to 4 to 24 hours, or from 6 to 12 hours to form a dried catalyst. In terms or ranges, the heating or drying step preferably occurs at a temperature ranging from 100 to 225° C., e.g., from 120° C. to 200° C.

Once impregnated and preferably after the drying step, the impregnated support preferably is heated under reducing atmosphere at elevated temperature in a reducing step. In the reducing step, any remaining cationic metal components in the impregnated catalyst are reduced to their elemental form. In a preferred embodiment, the impregnated catalyst is subjected to a reducing atmosphere comprising a hydrogen/inert gas mixture, preferably at a hydrogen concentration of from 5 to 20 mol % hydrogen, e.g., from 5 to 15 mol % hydrogen or most preferably about 10 mol % hydrogen, the remainder being an inert gas such as nitrogen. The temperature profile of the reducing step may vary widely. In a preferred embodiment, the reduction step begins at room temperature and is gradually ramped to a maximum reduction temperature, which, for example, may range from 225° C. to 500° C., e.g., from 280° C. to 350° C., most preferably about 300° C. The ramping may occur at a rate of from 0.5° C./min to 5° C./min, preferably from 1 to 3° C./minute or about 2° C./minute. Once the maximum temperature is achieved, the impregnated catalyst preferably is held at the maximum temperature for from 1 to 12 hours, e.g., from 4 to 8 hours or about 6 hours. Alternatively, the dried impregnated catalyst is put in an oven and heated to the maximum temperature substantially without a ramping profile.

Since oxalates decompose at relatively low temperatures, they typically can be removed from the catalyst during the drying and/or reducing steps. Thus, one advantage of employing oxalate precursors is that a separate calcination step may be avoided. Although not necessary, in some embodiments, it may be desired to calcine the dried catalyst in order, for example, to remove any other components derived from one or more additional metal precursors that are not desired in the final catalyst composition. Calcination may be desired, for example, if one or more additional precursors, for example one or more metal nitrates or metal acetates, are employed either in the mixed metal precursor or in a metal precursor solution that is separate from the mixed metal precursor. Thus, in one embodiment, the process further comprises the step of calcining the reduced catalytic components on the support. The calcining step preferably comprises heating the dried and preferably reduced catalyst to a temperature greater than the temperatures employed in the drying and reducing steps. For example, the dried and reduced catalyst optionally may be heated to a maximum calcination temperature greater than 225° C., e.g., greater than 300° C., greater than 400° C. or greater than 500° C. In terms of ranges, the maximum calcination temperature optionally ranges from 225° C. to 600° C., e.g., from 300 to 600° C. or from 400° C. to 600° C. The calcination step may occur for a period of time ranging from 1 to 12 hours, e.g., from 4 to 8 hours.

In some optional embodiments, one or more separate metal precursors are used to impregnate the support in addition to the mixed metal precursor. This may be desired, for example, in order to incorporate in the catalyst one or more metals that are less electropositive tin(II), or that have a standard reduction potential less than 0.15 eV. If employed, the separate metal precursor preferably comprises an additional metal precursor comprising an additional metal, and a liquid carrier, e.g., water. The one or more additional metals optionally are selected from the group consisting of Group IB, IIB, IIIB, IVB, VB, VIIB, VIIB, or VIII transitional metal, a lanthanide metal, an actinide metal or a metal from any of Groups IIIA, IVA, VA, or VIA. For example, the one or more additional metals optionally are selected from the group consisting of copper, iron, cobalt, nickel, ruthenium, rhodium, palladium, osmium, iridium, platinum, titanium, zinc, chromium, molybdenum, and tungsten. This approach may be used, for example, as an alternative means to form a trimetallic catalyst, such as any of those listed in Table 1, above.

In this embodiment, the separate metal precursor may be added to the support before, after or simultaneously to the mixed metal precursor. If the separate metal precursor and the mixed metal precursor are sequentially added to the support, it is preferred to dry and optionally reduce and/or calcine the support between impregnation steps. This embodiment may be desired, for example, in order to form a catalyst having a layered catalytic structure. For example, if the mixed metal precursor is impregnated first, the support dried and reduced and optionally calcined, followed by impregnation with a separate metal precursor, then the resulting catalyst may have a layered structure comprising a support core, an inner layer comprising tin and the second metal (or oxide thereof), and an outer layer comprising the metal or metal oxide derived from the separate metal precursor.

Optionally, the processes for forming catalysts according to the present invention may further comprise one or more additional steps such as, but not limited to, fixing the catalytic components on the support material, and/or washing the fixed catalytic components. In addition, some steps may be repeated and the order of the steps may be different from that listed above (e.g. the reducing step may precede the fixing step).

In one embodiment, in the impregnating step, the volume of mixed metal precursor is selected so that it corresponds to between 50% and 150%, e.g., between 85% and 110% or between 85% and 100%, of the pore volume of the support material. Volumes between about 95% and about 100% of the pore volume of the support material are preferred.

Typically, before impregnation, the support is dried, e.g., at a temperature ranging from 100° C. to 150° C., preferably about 120° C., and shaped to particles having size distribution in the range of 0.1 to 1.0 mm, e.g., from 0.2 to 0.6 mm, from 0.2 to 0.4 mm, or from 0.2 to 0.3 mm. Optionally, the supports may be pressed, crushed, and/or sieved to the desired size distribution. Any of the known methods to shape the support materials into desired size distribution may be employed. In addition, the fixing, washing, reducing, and activating steps may be performed in accordance with methods well known in the art. Examples of each of these steps are, for example, disclosed in U.S. Pat. No. 7,518,014, which is hereby incorporated by reference in its entirety.

The structure and morphology of the metals as disposed on the support in the formed catalyst may vary. For example, the particles may be disposed as an alloy, e.g., a homogeneous alloy, on the support, e.g., not as individual particles of individual metals. That is, the crystalline structure of the impregnated particles may contain both tin and second metal molecules. In one embodiment, tin and second metal, e.g., platinum, are homogeneously distributed on the support. In another embodiment, the metals on the support are disposed in a non-layered manner. In some multiple-step impregnation methods involving the mixed metal precursor and one or more additional metal precursors, impregnation of the mixed metal precursor may result in a layer of the first metal and subsequent impregnation step(s) may result in addition layer(s) atop the first layer.

The final composition of the catalyst depends on the relative amounts of tin oxalate and second metal precursor employed as well as whether additional metal precursors are employed, either in the mixed metal precursor or in one or more separate metal precursors. The resultant catalyst, in one embodiment, comprises tin in an amount from 0.1 to 10 wt %, e.g. from 0.3 to 5 wt %, or from 0.5 to 3 wt %, or optionally in an amount greater than 0.1 wt %, e.g., greater than 5 wt % or greater than 1 wt %. The catalyst also preferably comprises the second metal in an amount from 0.1 and 20 wt %, e.g., from 0.3 to 10 wt %, or from 0.5 to 5 wt %, or optionally in an amount greater than 0.1 wt %, e.g., greater than 1 wt % or greater than 5 wt %. The mole ratio of the tin to the second metal in the catalyst preferably is from 10:1 to 1:10, e.g., from 4:1 to 1:4, from 2:1 to 1:2, from 1.5:1 to 1:1.5 or from 1.1:1 to 1:1.1. Generally, a tin to second metal ratio of about 1:1 provides desired stoichiometry for the redox reaction to form nanoparticles of the second metal, as discussed above. In addition, if the second metal is platinum, providing a Sn/Pt molar ratio on the order of 1:1 has now been shown to yield acetic acid hydrogenation catalysts that are highly selective to the formation of ethanol. The tin and the second metal, e.g., Pt, may be alloyed with one another or may comprise a non-alloyed metal solid solution or mixture.

Generally, the total weight of all metals (including additional metals, if any, other than tin and the second metal) present in the catalyst preferably is from 0.1 to 25 wt %, e.g., from 0.5 to 15 wt %, or from 0.75 wt % to 10 wt %. Where the catalyst comprises only tin and a second metal, the tin preferably is present in an amount from 0.1 wt % to 5 wt. %, e.g., from 0.3 wt % to 5 wt %, and the second metal preferably is present in an amount from 0.1 wt % to 10 wt. %, e.g., from 0.5 wt % to 5 wt %. In addition to the tin and the second metal, the catalyst may further comprise one or more additional metals as discussed above. Where the catalyst comprises additional metals (i.e., metals other than tin and the second metal), the additional metals preferably are present in an amount from 0.1 wt % to 3 wt. %, e.g., from 0.2 wt % to 2 wt %. For purposes of the present specification, unless otherwise indicated, weight percent is based on the total weight the catalyst including all metals and support. The metals in the catalyst may be present in the form of one or more elemental metals, one or more metal oxides, or a combination of the two. For purposes of determining the weight percent of the metal(s) in the catalyst, the weight of any oxygen that is bound to the metal is ignored.

Supports

The catalytic metals of the present invention generally will be carried on and/or within a support. Suitable supports include materials that are substantially uniform in identity or a mixture of materials. Overall, the support may be generally inert to the reaction being performed. The support may be composed of any suitable substance preferably selected so that the support has a relatively high surface area per unit mass or volume, such as a porous structure, a molecular sieve structure, a honeycomb structure, or other suitable structure. For example, the support may comprise silica, alumina, silica-alumina, titania, titano-silicate, zirconia, zircono-silicate, niobia, silicates, alumino-silicates, titanates, spinel, silicon carbide, silicon nitride, carbon, cordierite, steatite, bentonite, clays, metals, glasses, quartz, pumice, zeolites, non-zeolitic molecular sieves, combinations thereof, and the like. Any of the different crystalline form of the materials may also be suitable, e.g., alpha or gamma alumina. Zirconia, zircono-silicates and titano-silicates containing support materials may also be employed. In addition, multilayer support materials are also suitable for use in the present invention.

The support in the catalyst of this invention may be composed of particles having any of various regular or irregular shapes, such as spheres, tablets, cylinders, discs, rings, stars, or other shapes. The support may have dimensions such as diameter, length or width of 1 mm to 10 mm, e.g., from 3 mm to 9 mm, or from 3 mm to 8 mm. Preferably, the particles largest dimension is from 2 mm to 9 mm, e.g., from 4 mm to about 8 mm or from 4 mm to 7 mm. In other instances, a ground or powder support may be suitable. As such, the support may have a regular or irregular shape with a diameter of between 10 microns and 1000 microns, e.g., between 10 microns and 700 microns or between 180 microns and 450 microns. Larger or smaller sizes may be employed, as well as polydisperse collections of particles sizes. For example, for a fluid bed catalyst, a preferred size range would include from 10 microns to 200 microns, e.g., from 10 microns to 150 microns or from 25 microns to 100 microns. For precursors used in layered catalysts, a size range of 10 to 250 microns is preferred.

Surface areas available for supporting catalytic components, as measured by the BET (Brunauer, Emmett, and Teller) method, may generally be between 1 $m^2/g$ and 500 $m^2/g$, e.g., from 20 $m^2/g$ to 200 $m^2/g$ or from 25 $m^2/g$ to 50 $m^2/g$. Also, for a porous support, the pore volume of the support material may generally range from 0.1 ml/g to 2 ml/g, e.g., from 0.4 ml/g to 1.2 ml/g or from 0.5 ml/g to 1.0 ml/g. An average pore size in the range, for example, of from 10 angstroms to 5000 angstroms, e.g., from 50 angstroms to 2000 angstroms or from 100 to 1000 angstroms, is desirable.

In preferred embodiments, the support is a silicaceous support selected from the group consisting of silica, pyrogenic silica, high purity silica, a calcium silicate such as calcium metasilicate, and mixtures thereof. In the case where silica is used as the silicaceous support, it is beneficial to ensure that the amount of alumina, which is a common contaminant for silica, is low, preferably under 1 wt %, e.g., under 0.5 wt % or under 0.3 wt %, based on the total weight of the support. In this regard, pyrogenic silica is preferred as it commonly is available in purities exceeding 99.7 wt %. High purity silica, as used throughout the application, refers to silica in which acidic contaminants such as alumina are present, if at all, at levels of less than 0.3 wt %, e.g., less than 0.2 wt % or less than 0.1 wt %. A preferred support, as discussed below, is calcium metasilicate-modified silica. When calcium metasilicate is used as a support modifier, it is not necessary to be quite as strict about the purity of the silica used although alumina is undesirable and will not normally be added intentionally. The alumina content of such silica, for example, may be less than 10 wt %, e.g., less than 5 wt % or less than 3 wt %. In cases where the support comprises a support modifier in the range of from 2% to 10%, larger amount of acidic impurities, such as alumina, can be tolerated so long as they are counterbalanced by an appropriate amount of a support modifier. In one embodiment of the invention, the surface area of the silicaceous support is at least about 100 $m^2/g$, e.g., at least about 150 $m^2/g$, at least about 200 $m^2/g$ or most preferably at least about 250 $m^2/g$. High surface area silica, as used throughout the application, refers to silica having a surface area of at least about 250 $m^2/g$.

Examples of suitable commercial silicaceous supports include KA160 from Sud Chemie, SS61138 High Surface Area (HSA) Silica Catalyst Carrier from Saint Gobain N or Pro, Aerolyst® 350 from Degussa, and other pyrogenic silicas with a particle size of 1 mm to 25 mm e.g., from 1 mm to 10 mm and low microporosity. The Saint-Gobain N or Pro SS61138 silica contains approximately 95 wt % high surface area silica; a surface area of 250 $m^2/g$; a median pore diameter of 12 nm; a total pore volume of 1.0 $cm^3/g$ as measured by mercury intrusion porosimetry and a packing density of about 352 $kg/m^3$.

Examples of suitable zirconia-containing supports include those from N or Pro, Zirconia Sales (America), Inc., Daichi Kigenso Kagaku Kogyo, Engelhard and Magnesium Elektron Inc (MEI). Suitable zirconia support materials have a wide range of surface areas from less than 5 $m^2/g$ to more than 300 $m^2/g$. Preferred zirconia supports have surface areas from 20 $m^2/g$ to 150 $m^2/g$, e.g., from 30 $m^2/g$ and about 100 $m^2/g$ more preferred. Supports, in one embodiment, may have their surfaces treated through a calcining step in which the virgin support material is heated. The heating reduces the surface area of the support material (e.g. calcining). This provides a method of creating support materials with specific surface areas that may not otherwise be readily available from suppliers.

Examples of other suitable supports include titano-silicates from Grace such as SP18-9534 (silica with 0.61% $TiO_2$) or zircono-silicates from Grace such as SP189043 (silica with 1.69% $ZrO_2$). More generally, suitable supports may include up to 70 wt % $TiO_2$, e.g., up to 50 wt % $TiO_2$ or up to 40 wt % $TiO_2$; or from 0.01 wt % to 75 wt % $TiO_2$, e.g., from 0.1 wt % to 50 wt % $TiO_2$, or from 0.1 wt % to 5 wt % $TiO_2$. Also, suitable support materials may include up to 70 wt % $ZrO_2$, e.g., up to 50 wt % $ZrO_2$ or up to 40 wt % $ZrO_2$; or from 0.01 wt % to 75 wt % $ZrO_2$, e.g., from 0.1 wt % to 50 wt % $ZrO_2$, or from 0.1 wt % to 5 wt % $ZrO_2$.

In another embodiment, it is contemplated to utilize a combination of support materials, each with a different characteristic. For example, at least two support materials, e.g., titania and silica, with different characteristics may exhibit different activities and selectivities, e.g., ethanol selectivities, thus permitting preparation of catalysts with a desired set of characteristics. Also, in one embodiment, plural different supports may be employed in a layered configuration as discussed in U.S. Patent Publication 2005/0181940, which is hereby incorporated by reference in its entirety. Additional techniques are known for creating layered support materials includes those described in U.S. Pat. Nos. 7,518,014; 6,486,370; 5,935,889; and 5,200,382, each of which is incorporated by reference in its entirety.

Modification of Support

In embodiments where substantially pure ethanol is to be produced at high selectivity, controlling the acidity of the support can be quite beneficial by incorporating a support modifier. One possible byproduct of the hydrogenation of acetic acid is ethyl acetate. It has now been discovered that in addition to the metal precursors and preparation conditions employed, metal-support interactions may have a strong impact on selectivity, e.g., selectivity to ethanol, over other hydrogenation products such as ethyl acetate.

In one embodiment, the support includes a support modifier that reduces the number of Brønsted acid sites on the support material and improving selectivity to ethanol over other reaction products. The support preferably includes a support modifier that is effective to suppress production of ethyl acetate, highly selectivity to ethanol, and possesses a low selectivity toward conversion of acetic acid to highly undesirable by-products such as methane, ethane and $CO_2$. The acidity of the support ideally is controlled such that less than 4%, preferably less than 2% and most preferably less than about 1% of the acetic acid is converted to ethane. In addition, the acidity of the support can be controlled by using a pyrogenic silica or high purity silica.

In one embodiment, the support comprises a metasilicate such as calcium metasilicate. If the support comprises silica, the support modifier, e.g., calcium metasilicate, preferably is present in an amount effective to reduce or balance Brønsted acid sites resulting from any residual alumina in the silica. Preferably, the calcium metasilicate is present in an amount from 1 wt % to 10 wt % to ensure that the support is essentially neutral or basic in character. As the calcium metasilicate tends to have lower surface area, in one embodiment the silicaceous support includes at least about 10 wt % high surface area silica.

The modification of the support with a support modifier to form a modified support may occur before, after, or concurrently with the metal impregnation step(s). In various optional embodiments, the support modifier may be, for example, selected from the group consisting of: (i) alkaline earth oxides, (ii) alkali metal oxides, (iii) alkaline earth metasilicates, (iv) alkali metal metasilicates, (v) Group IIB oxides, (vi) Group IIB metasilicates, (vii) Group IIIB oxides, (viii) Group IIIB metasilicates, and mixtures of any of (i)-(viii). The support modifier preferably is a basic non-volatile stabilizer-modifier. Preferably, the support modifier is selected from the group consisting of oxides and metasilicates of sodium, potassium, magnesium, calcium, scandium, yttrium, and zinc as well as precursors therefor and mixtures of any of the foregoing. A particularly preferred support modifier is calcium metasilicate ($CaSiO_3$). Preferably $CaSiO_3$ is impregnated on a support, and a preferred modifier/support combination is $SiO_2/CaSiO_3$. The total weight of the modified support, which includes the support material and the support modifier, based on the total weight of the catalyst, preferably is from 25 wt % to 99.9 wt %, e.g., from 30 wt % to 97 wt %, or from 35 wt % to 95 wt %. In one embodiment, the support modifier preferably is provided in amount to reduce the amount active Brønsted acid sites in the support and preferably to ensure that the surface of the support is substantially free of active Brønsted acid sites. Unless the context indicates otherwise, the acidity of a surface or the number of acid sites thereupon may be determined by the technique described in F. Delannay, Ed., "Characterization of Heterogeneous Catalysts"; Chapter III: Measurement of Acidity of Surfaces, p. 370-404; Marcel Dekker, Inc., N.Y. 1984, the entirety of which is incorporated herein by reference.

In other embodiments, the modifier also may be a metal selected from alkali metals, alkaline earth metals, transition metals, and lanthanides. In other embodiments, the modifier is selected from Group I to Group VI elements. Of these elements, barium, magnesium, cerium, potassium, calcium, niobium, tantalum, titanium, yttrium, strontium, zirconium, lanthanum, praseodymium, vanadium, molybdenum, and rubidium are more preferred, with zirconium being slightly less preferred. Combinations of these elements are also suitable with binary combinations the preferred type of combination. For example, suitable binary combinations include Ti—Zr, Mg—Nb, Nb—Zr, Mg—Ti, Nb—Ti, Mg—Zr or the like. Ratios of metals in the binary combinations range from 10:1 to 1:10, e.g., from 4:1 to 1:4. It is noted that the modification or modifier impregnation is considered separate from metal impregnation. Thus, a metal impregnation that involves one step, e.g., using the inventive metal precursors, and which also includes support modification would still be considered a one step metal impregnation.

In addition, redox or acidic support modifiers may be used, particularly if high selectivities to hydrogenation products other than ethanol, such as ethyl acetate, are desired. Suitable redox and acidic modifiers are selected from the group consisting of: oxides of Group IVb metals, oxides of Group Vb metals, oxides of Group VIb metals, iron oxides, aluminum oxides, and mixtures thereof. These support modifiers are redox or acid non-volatile stabilizer-modifiers. Optional redox support modifiers are selected from the group consisting of $WO_3$, $MoO_3$, $Fe_2O_3$, and $Cr_2O_3$. Optional acidic support modifiers may be selected from the group consisting of $TiO_2$, $ZrO_2$, $Nb_2O_5$, $Ta_2O_5$, and $Al_2O_3$.

In preferred embodiments, the support modifier is present in an amount from 0.01 wt % to 50 wt %, e.g., 0.1 wt % to 50 wt %, from 0.2 wt % to 25 wt %, from 0.5 wt % to 15 wt %, or from 1 wt % to 8 wt %, based on the total weight of the catalyst.

Supports are typically modified before the metal precursors (the tin oxalate and second metal precursor and any additional metal precursors) are added to the support material. In one preferred embodiment, a support material is impregnated with one or more aqueous solutions of the modifiers (referred to as modifier precursor solutions). The physical state of the support material during the contacting step may be a dry solid, a slurry, a sol-gel, a colloidal suspension or the like.

In one embodiment, the modifiers may be contained in the metal precursor. As such the modifiers may be the water soluble salts thereof. These include, but are not limited to, chlorides, other halides, nitrates, nitrites, hydroxides, oxides, lactates, acetates (OAc), ammoniums and amines, with halide (e.g., chloride) free salts being preferred, with lactates, oxalates, acetates, and nitrates being most preferred. Examples of modifier salts suitable for use in modifier precursor solutions include $Ba(NO_3)_2$, $Mg(NO_3)_2 \cdot 6H_2O$, $Ce(NO_3)_3 \cdot 6H_2O$, $KNO_3$, $Ca(NO_3)_2 \cdot 4H_2O$, $(NH_4)_{1.35}Nb(C_2O_4)_{2.73}$, $Ta(C_2O_4)_{2.5}$, $Ti(CH_3CH(O-)CO_2NH_4)_2(OH)_2$, $Y(NO_3)_3 \cdot 6H_2O$, $ZrO(NO_3)_2 \cdot xH_2O$.

Furthermore, more than one salt may be used in a given modifier precursor solution. Precursor solutions typically may be made by dissolving the selected salt or salts in water, with or without solubility modifiers such as acids, bases or other solvents. Other non-aqueous solvents may also be suitable.

The modifier precursor solutions may be impregnated onto the support material in a single impregnation step, although support materials may be impregnated multiple times with modifiers having low atomic weight (e.g. Mg) or limited solubility in water (e.g. Nb or Ba). If multiple modifiers are utilized, the impregnation may be simultaneous (e.g. co-impregnation) or sequential and support material may be impregnated through the use of one or multiple precursor solutions.

As one example, the support modifier, e.g., $CaSiO_3$, is added to the support material, e.g., $SiO_2$. For example, an aqueous suspension of the support modifier may be formed by adding the solid support modifier to deionized water, followed by the addition of colloidal support material thereto. The resulting mixture may be stirred and added to additional support material using, for example, incipient wetness techniques in which the support modifier is added to a support material having the same pore volume as the volume of the support modifier solution. Capillary action then draws the support modifier into the pores in the support material. The modified support can then be formed by drying and calcining to drive off water and any volatile components within the support modifier solution and depositing the support modifier on the support material. Drying may occur, for example, at a temperature of from 50° C. to 300° C., e.g., from 100° C. to 200° C. or about 120° C., optionally for a period of from 1 to 24 hours, e.g., from 3 to 15 hours or from 6 to 12 hours. Once formed, the modified supports may be shaped into particles having the desired size distribution, e.g., to form particles having an average particle size in the range of from 0.2 to 0.4 cm. The supports may be extruded, pelletized, tabletized, pressed, crushed and sieved to the desired size distribution. Any of the known methods to shape the support materials into desired size distribution can be employed. Calcining of the shaped modified supports may occur, for example, at a temperature of from 250° C. to 800° C., e.g., from 300 to 700° C. or about 500° C., optionally for a period of from 1 to 12 hours, e.g., from 2 to 10 hours, from 4 to 8 hours or about 6 hours.

One advantage of catalysts of the present invention is increased activity of the catalyst. Accordingly, it can be appreciated that the catalysts of the present invention are fully capable of being used in commercial scale industrial applications for hydrogenation of acetic acid, particularly in production of ethanol. In particular, it is possible to achieve such a degree of stability that catalyst activity will decline by less than 10% over periods of at least one week (168 hours), at least two weeks (336 hours) or at least three weeks (504 hours). In one another embodiment, the catalyst activity will decline by less than 5% over periods of at least 168 hours, at least 336 hours or at least 504 hours. The catalyst activity may also be determined by the stability after initial startup of the reactor. After the startup, typically up to 10 hours, up to 20 hours or up to 25 hours, the catalyst may decline by less than 5% over periods of a at least 168 hours, at least 336 hours or at least 504 hours. In further embodiments, after startup, the catalyst may decline by less than 3% over periods of a at least 168 hours, at least 336 hours or at least 504 hours.

In a preferred embodiment, when the catalyst support comprises high purity silica, with calcium metasilicate as a support modifier, the catalyst activity may extend, or stabilize, the activity and selectivity of the catalyst for prolonged periods of time, for example, extending beyond four weeks, and even months, of commercially viable operation in the presence of acetic acid vapor at temperatures of 125° C. to 350° C. and at space velocities of over 2500 $hr^{-1}$.

The invention also relates to a method for direct formation of ethanol and/or ethyl acetate from acetic acid using the inventive catalyst. The method includes contacting acetic acid and hydrogen with the inventive catalyst. The reaction may be conducted under conditions sufficient to hydrogenate the acetic acid. Examples of such conditions are discussed in U.S. patent application Ser. Nos. 12/221,141 and 12/221,239, each of which is incorporated by reference in its entirety.

Embodiments of the invention will become more evident in view of the following non-limiting examples

EXAMPLES

Preparation of Hydrogenation Catalysts

The following materials were utilized in the Examples:
(a) Platinum oxalate, $PtC_2O_4$, (solution, 13.638 wt % Pt) from Heraeus.
(b) Tin(II) oxalate, $SnC_2O_4$ and ammonium oxalate monohydrate,
(c) $(NH_4)_2C_2O_4 \cdot H_2O$ purchased from Aldrich and used without further purification.

A modified silica support (HSA SS #61138, SA=250 $m^2/g$) from N or Pro Saint Gobain, $SiO_2$—$CaSiO_3$(6), having 6 wt % $CaSiO_3$ was dried at 120° C. under circulating air overnight prior to use.

A mixed metal precursor was prepared as follows. 1.62 g (11.38 mmol) of solid ammonium oxalate monohydrate was added to 50 ml of deionized $H_2O$ and dissolved with stirring at room temperature. 0.94 g (4.55 mmol) of tin(II) oxalate was added to the ammonium oxalate solution. The resultant mixture was stirred for another ten minutes at room temperature yielding a slightly opaque, colorless solution. 6.51 g of the platinum(II) oxalate solution (13.638 wt % Pt) was diluted to a total volume of 18 ml using deionized $H_2O$. The dark blue platinum solution was then added to the ammonium/tin(II) solution with stirring resulting in a yellow-brown, homogeneous solution. The solution was stirred for twenty minutes at room temperature.

The mixed metal precursor was added to the modified silica support ($SiO_2$—$CaSiO_3$(6)) having a 3 mm pellet shape using the incipient wetness technique. The material was left standing for one hour at room temperature, and then evacuated to dryness in a rotor evaporator, at a slow/minimum rotation bath temperature of 80° C. The material was then dried at 120° C. overnight under circulating air.

The catalyst was then reduced using a $H_2/N_2$ mixture with 10 mol % of $H_2$ (total flow~275 sccm/min at atmospheric pressure) and the following temperature program:
(a) Room temperature to 300° C. at a 2 deg/min ramp,
(b) Hold at 300° C. for 6 hrs.
(c) Cool down to room temperature (the catalyst may alternatively be cooled to reaction temperature, if done in situ in the reactor prior to testing).

The resultant catalyst was utilized to hydrogenate acetic acid as follows.

At room temperature and 200 psig (14 bar) pressure, 0.18 g/min of acetic acid and 683 sccm/min $H_2$ (no $N_2$ dilutant) were fed to a reactor at GHSV~4700 $h^{-1}$. The reactor contained 10 ml solid catalyst (⅛ inch extrudates, diluted 1:1 v/v with 3 mm glass beads). Reaction time was 48 hrs.

The product stream showed a 55% conversion of acetic acid with the following product selectivities:
89 wt. % ethanol
6 wt. % ethyl acetate
3 wt. % acetaldehyde
2 wt. % diethylacetal.

As shown, the resultant catalyst contained, inter alia, tin, which is known to have an inability to solubilize in typical aqueous solvents. This catalyst, surprisingly and unexpectedly, was successfully produced using a mixed metal precursor comprising both aqueous solubilized tin and aqueous solubilized platinum in a one step impregnation method and without the use of halogenated metal precursors. Further, the preparation did not include a calcination step. The catalyst, when used in the hydrogenation of acetic acid, demonstrated a high conversion and a high selectivity to ethanol.

Any feature described or claimed with respect to any disclosed implementation may be combined in any combination with any one or more other feature(s) described or claimed with respect to any other disclosed implementation or implementations, to the extent that the features are not necessarily technically incompatible, and all such combinations are within the scope of the present invention. Furthermore, the claims appended below set forth some non-limiting combinations of features within the scope of the invention, but also contemplated as being within the scope of the invention are all possible combinations of the subject matter of any two or more of the claims, in any possible combination, provided that the combination is not necessarily technically incompatible.

We claim:

1. A process for producing a catalyst, the process comprising the steps of:
    (a) contacting a support with a mixed metal precursor solution comprising tin oxalate, a second metal precursor to a second metal, a solubilizing agent, and water to form an impregnated support; and
    (b) heating the impregnated support under conditions effective to remove at least a weight majority of the water and reduce the tin from the tin oxalate and the second metal from the second metal precursor and form the catalyst;
    wherein the support is selected from the group consisting of iron oxide, silica, titania, zirconia, magnesium oxide, calcium silicate, carbon, graphite, high surface area graphitized carbon, activated carbons, and mixtures thereof;
    wherein the support comprises a support modifier selected from the group consisting of an acid support modifier and a redox support modifier and
    wherein the catalyst is a hydrogenation catalyst.

2. The process of claim 1, wherein the second metal precursor comprises a second metal oxalate.

3. The process of claim 1, wherein the second metal is platinum and the second metal precursor comprises platinum oxalate.

4. The process of claim 1, wherein the second metal is selected from the group consisting of iridium, rhodium, palladium, copper, cobalt, manganese, lead, chromium, thallium, iron, osmium, gold, silver, cadmium, rhenium, rhodium, and ruthenium.

5. The process of claim 1, wherein the heating step occurs under a reducing atmosphere at least in part.

6. The process of claim 1, wherein the heating step comprises a drying step and a reducing step.

7. The process of claim 1, further comprising the step of:
    (c) forming the mixed metal precursor by combining the tin oxalate, the second metal precursor, the solubilizing agent and the water.

8. The process of claim 1, wherein the contacting comprises contacting through incipient wetness techniques.

9. The process of claim 1, wherein the mixed metal precursor comprises the tin oxalate at a theoretical concentration of from 0.01 M to 0.1 M, the second metal precursor at a theoretical concentration of from 0.01 M to 0.1 M, and the solubilizing agent at a theoretical concentration of from 0.02 M to 0.32 M.

10. The process of claim 1, wherein the mixed metal precursor comprises the solubilizing agent and the tin oxalate at a molar ratio greater than 1:1.

11. The process of claim 1, wherein the mixed metal precursor comprises the tin oxalate, the second metal precursor, and the solubilizing agent in solution.

12. The process of claim 1, wherein the contacting is performed in a single step.

13. The process of claim 1, wherein the mixed metal precursor is at a temperature ranging from 20° C. to 30° C. during the contacting step.

14. The process of claim 1, wherein the redox support modifier is selected from the group consisting of $WO_3$, $MoO_3$, $Fe_2O_3$, $Cr_2O_3$ and combinations thereof.

15. The process of claim 1, wherein the heating is to a temperature from 120° C. to 200° C.

16. The process of claim 1, further comprising calcining the catalyst at a temperature from 225° C. to 500° C. to form a calcined catalyst.

17. The process of claim 1, further comprising:
    (c) contacting the support with a third metal precursor comprising a third metal not tin and different from the second metal; and
    (d) reducing the third metal precursor to form the third metal or its oxide on the support.

18. The process of claim 1, wherein the solubilizing agent is selected from the group consisting of sodium oxalate, potassium oxalate, ammonium oxalate, phosphonium oxalate, and combinations thereof.

19. The process of claim 1, wherein the support has a surface area of at least 200 $m^2/g$.

20. A process for producing a catalyst, the process comprising the steps of:
    (a) contacting a support with a mixed metal precursor solution comprising tin oxalate, a second metal precursor to a second metal, a solubilizing agent, and water to form an impregnated support; and
    (b) heating the impregnated support under conditions effective to remove at least a weight majority of the water and reduce the tin from the tin oxalate and the second metal from the second metal precursor and form the catalyst;
    wherein the support is selected from the group consisting of iron oxide, silica, titania, zirconia, magnesium oxide, calcium silicate, carbon, graphite, high surface area graphitized carbon, activated carbons, and mixtures thereof;
    wherein the solubilizing agent is selected from the group consisting of sodium oxalate, potassium oxalate, phosphonium oxalate, and combinations thereof; and
    wherein the catalyst is a hydrogenation catalyst.

* * * * *